United States Patent [19]

Kramer et al.

[11] Patent Number: 5,165,152
[45] Date of Patent: Nov. 24, 1992

[54] PROCESS AND APPARATUS FOR THE CONTINUOUS PRODUCTION OF ABSORBENT BODIES

[75] Inventors: Wolfgang Kramer, Hallein, Austria; Fritz Pesendorfer, Bad Honnef, Fed. Rep. of Germany; Gerhard Schwankhardt, Attnang-Puchheim, Austria

[73] Assignee: McNeil-PPC, Inc., Milltown, N.J.

[21] Appl. No.: 572,985

[22] PCT Filed: Jan. 3, 1990

[86] PCT No.: PCT/EP90/00008

§ 371 Date: Nov. 2, 1990

§ 102(e) Date: Nov. 2, 1990

[87] PCT Pub. No.: WO90/07314

PCT Pub. Date: Jul. 12, 1990

[30] Foreign Application Priority Data

Jan. 3, 1989 [AT] Austria ..................... 10/89

[51] Int. Cl.$^5$ ............................. A61F 13/22
[52] U.S. Cl. ...................................... 28/118
[58] Field of Search ................. 28/118, 119, 121; 604/904, 358, 379, 385.1; 156/184, 191, 193, 203

[56] References Cited

U.S. PATENT DOCUMENTS

| | | | |
|---|---|---|---|
| 2,444,528 | 7/1948 | Popper et al. | 28/118 |
| 3,716,430 | 2/1973 | Croon et al. | 28/118 |
| 3,845,520 | 11/1974 | Simon | 28/119 |
| 3,874,032 | 4/1975 | Simon et al. | 28/119 |
| 4,144,623 | 3/1979 | Steffens | 28/118 |
| 4,175,561 | 11/1979 | Hirschman | 28/118 |
| 4,642,108 | 2/1987 | Sustmann | 604/358 |
| 4,661,101 | 4/1987 | Sustman | 604/904 |
| 4,787,895 | 11/1988 | Stokes et al. | 604/358 |
| 4,816,100 | 3/1989 | Friese | 604/904 |
| 5,019,061 | 5/1991 | Hoden et al. | 604/385.1 |

Primary Examiner—Werner H. Schroeder
Assistant Examiner—Amy Brooke Vanatta

[57] ABSTRACT

The invention relates to a process and an apparatus for the continuous production of absorbent bodies (30) from a web of fiber material (40) which is folded longitudinally several times in a folding station (A) and which is surrounded in a guide tube (86) with a sheathing band (82), the longitudinal edges of which are connected to one another by means of a closing device. The web of fiber material (30) is thereafter fed to a press station (C) which consists of pairs of press and smoothing rollers arranged in close succession and offset at 90° relative to one another. By means of these press rollers, the web of fiber material (130) is rolled down in steps to or below the final cross-section of the absorbent body (30), to form a fleece rod (240). Subsequently, the absorbent bodies (30) are pinched by means of pinching rollers (334, 338) in a severing station (D) and are thereby preformed at the front end and thereafter fed to a forming device, by means of which the front ends of the absorbent bodies (30) are equipped with a round dome and the rear ends of the absorbent bodies (30) with a depression as an insertion aid, when the absorbent body (30) is to be used as a tampon for feminine hygiene. The process and the apparatus allow the high-speed mass production of absorbent bodies which, whilst using less material, make it possible to achieve a higher stability or buckling resistance of the absorbent bodies.

38 Claims, 10 Drawing Sheets

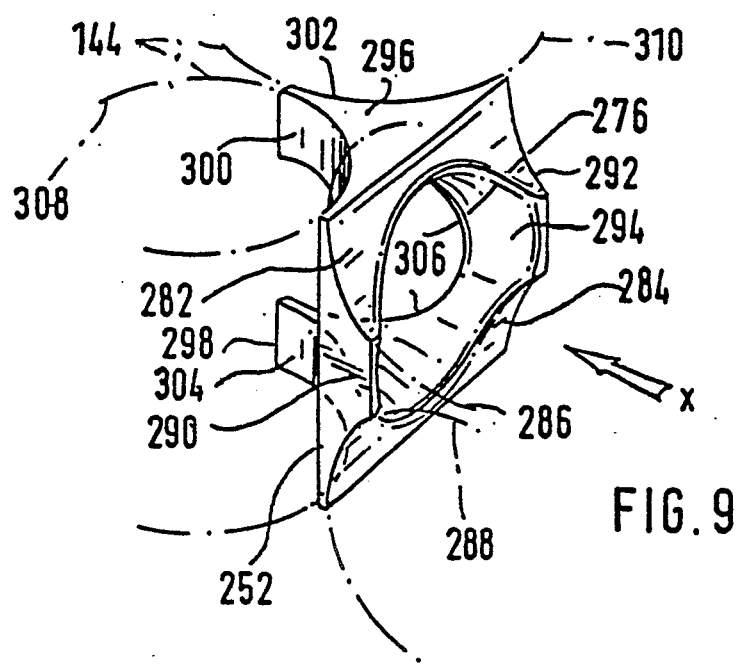
FIG. 9
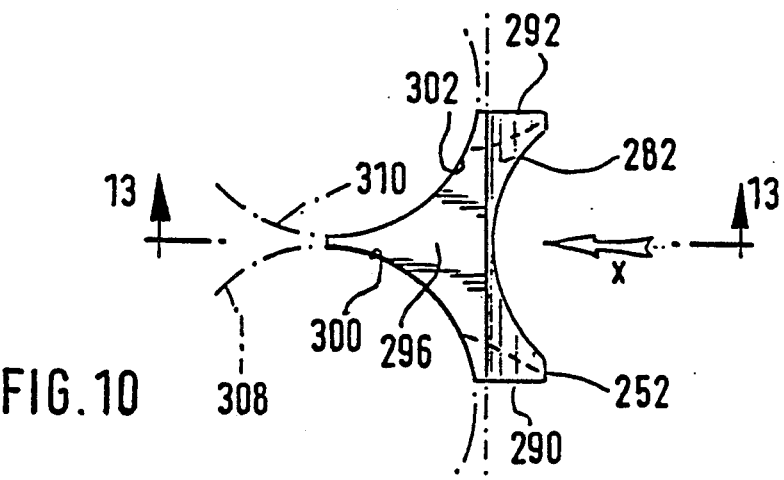
FIG. 10
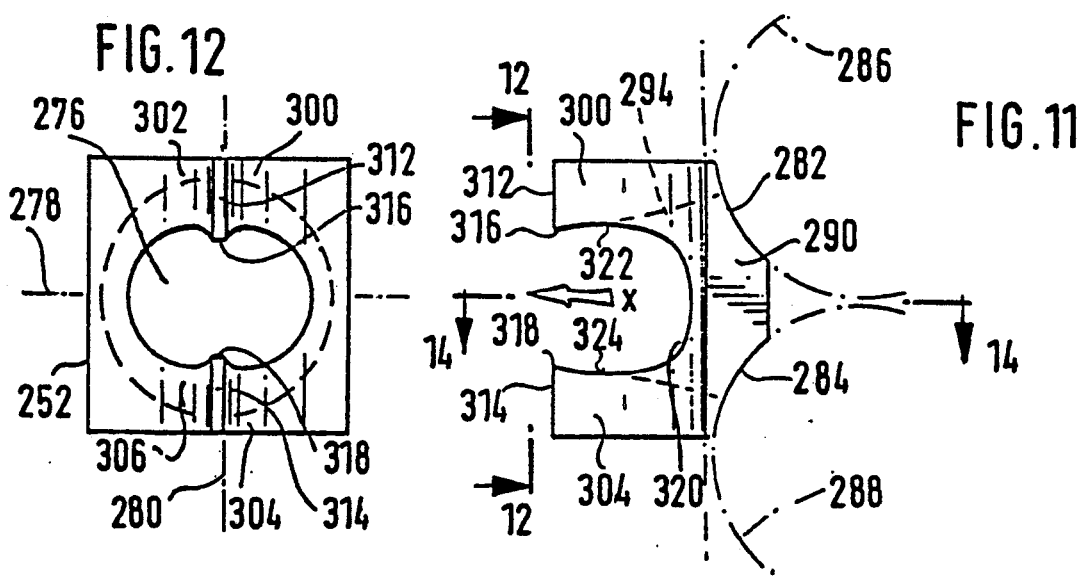
FIG. 12
FIG. 11

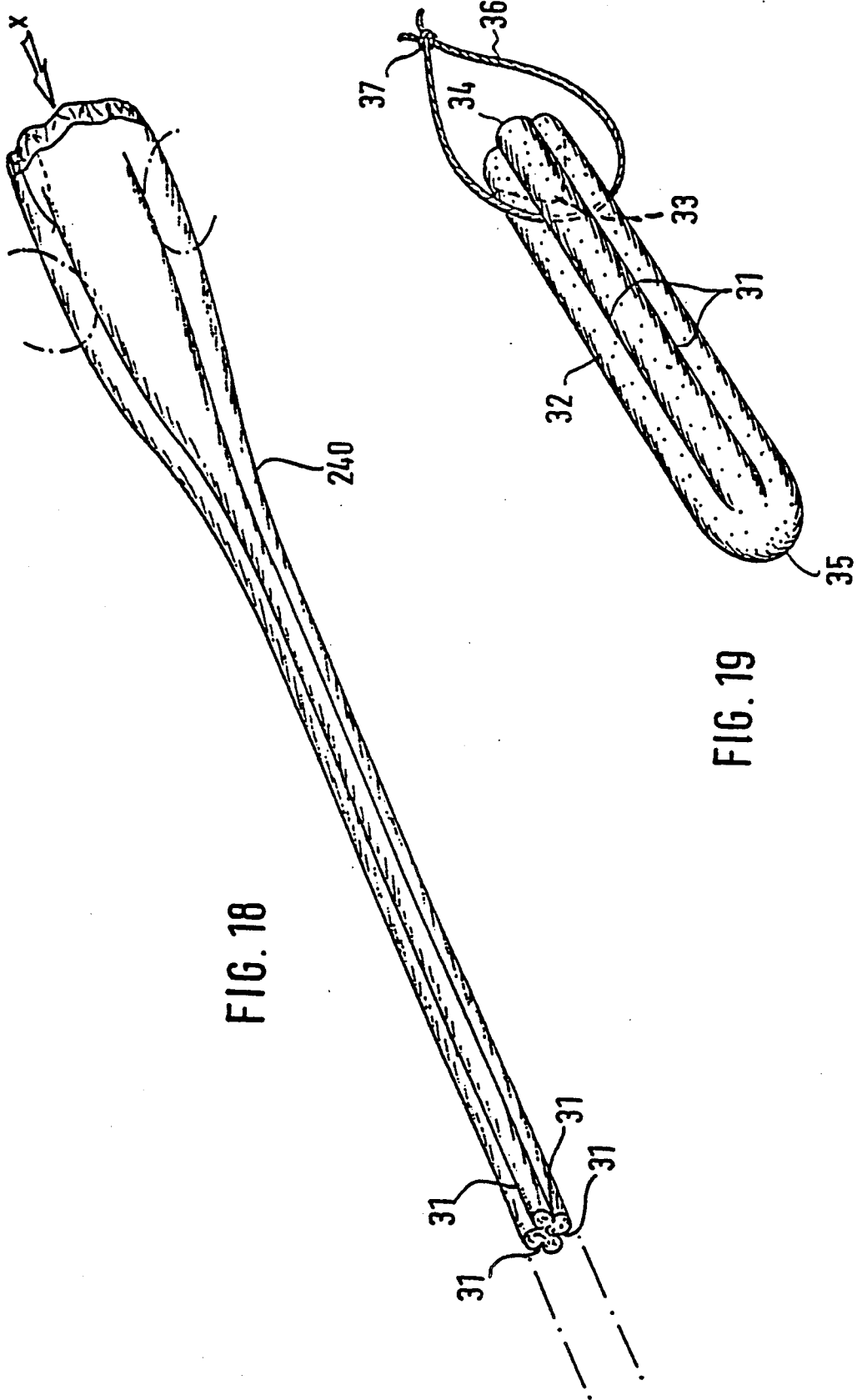

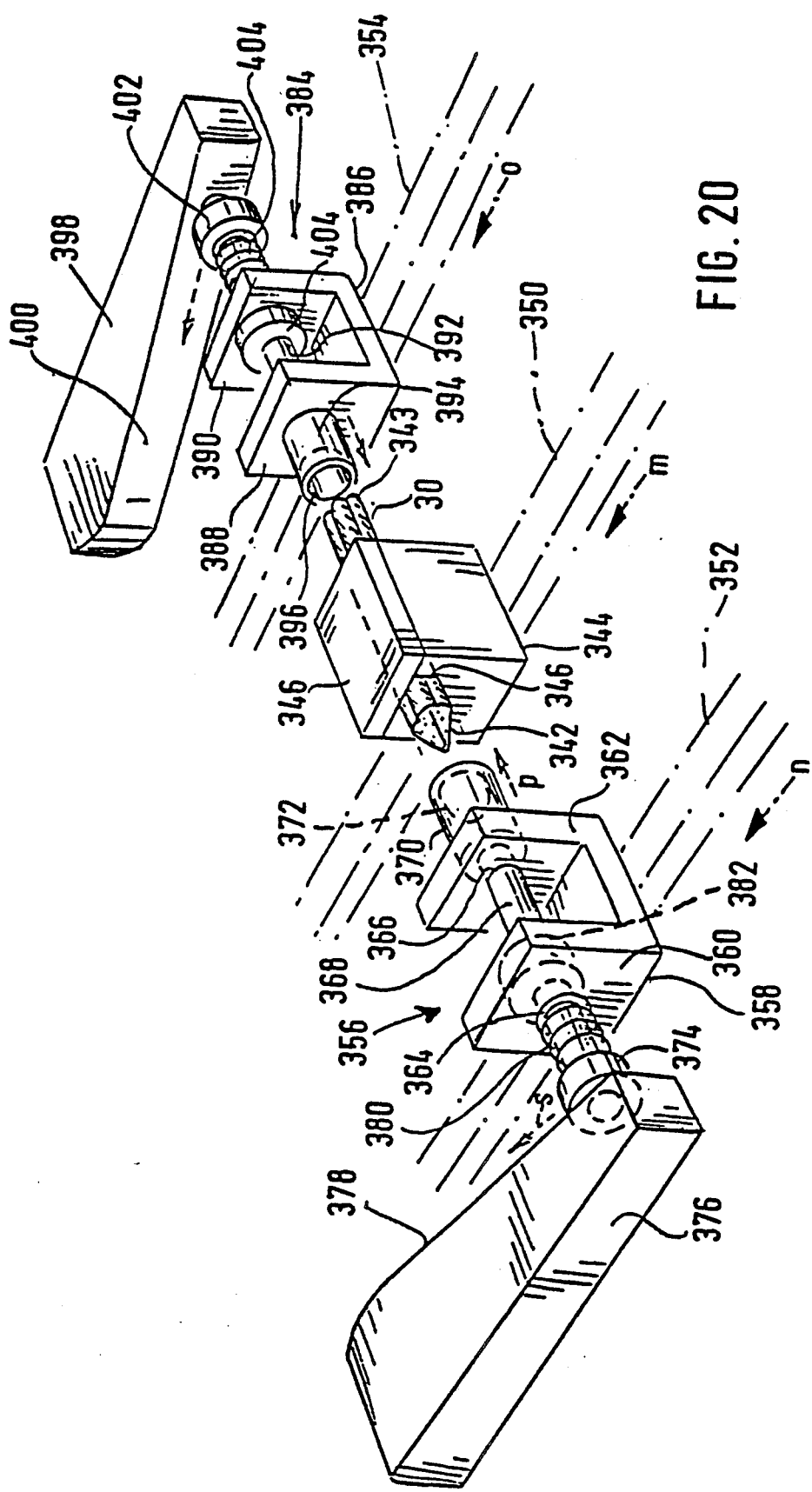

PROCESS AND APPARATUS FOR THE CONTINUOUS PRODUCTION OF ABSORBENT BODIES

The invention relates to a process and apparatus according to the pre-characterizing clauses of claims 41 and 60.

A process and an apparatus of the abovementioned generic type are known from Swiss Patent Specification 355,255. In this, a wad roll is folded on itself in the longitudinal direction and surrounded by a sheathing band, the mutually overlapping longitudinal sides of which are connected to one another by means of heated press rollers. The fibre rod is then severed into individual length portions which are thereupon pressed intermittently in a press to form tampons. The sheathing band at the same time forms the recovery band for the tampon.

A process and an apparatus are known from U.S. Pat. No. 3,523,535, and in these an air-placed wood-pulp layer is applied to a nonwoven sheathing band of viscose fibres and is fed between two conveyor belts to a nozzle-like die which gives the rod of material a circular cross-section The rod of material is thereafter guided over a table, above which are arranged a glue applicator device for closing the sheathing band and two press rollers which exert slight pressure on the rod of material in order to stabilize its form, before the rod is subsequently cut into individual tampon lengths.

The object on which the invention is based is to improve the process and apparatus for the continuous production of absorbent bodies according to the pre-characterizing clauses of Patent claims 1 and 21, in such a way as to obtain a high-speed process and a corresponding apparatus for the production of those absorbent bodies which are suitable particularly as tampons for feminine hygiene and which, whilst preserving essential properties of known tampons, have an increased stability or buckling resistance.

The invention achieves this object by means of the features mentioned in the characterizing clauses of Patent claims 1 and 21.

As a result of the invention, the properties of the absorbent bodies can easily be matched to their particular intended use. At the same time, it is guaranteed that the mass production of the absorbent bodies will be extremely economical, because it is continuous. The range of variation of the process according to the invention and of the apparatus according to the invention makes it possible, for instance, to apply a sheathing band to the absorbent body and to produce absorbent bodies with or without a different number of longitudinal grooves which, when the absorbent bodies are used as tampons, contribute considerably to increasing the stability and absorption rate of such tampons. These advantages are achieved even though all the operations of processing the fibre material take place continuously, that is to say at no time in the process is there any interruption in the work cycle or any intermittent processing.

The invention is explained in detail below by reference to the diagrammatic drawing of an exemplary embodiment of the apparatus according to the invention. In the drawing:

FIG. 9 shows a perspective rear view of a guide positioned between mutually adjacent pairs of rollers in the press station;

FIG. 10 shows a top view of the guide according to FIG. 9;

FIG. 11 shows a side view of the guide;

FIG. 12 shows a front view of the guide;

FIG. 18 shows a view of the fleece rod when it is subjected to compression, the rollers and guides having been removed for the sake of a clearer illustration;

FIG. 19 shows a perspective view of a finished absorbent body, and

FIG. 20 shows a perspective view of a device for the shaping the front and rear ends of an absorbent body.

Figure 1:
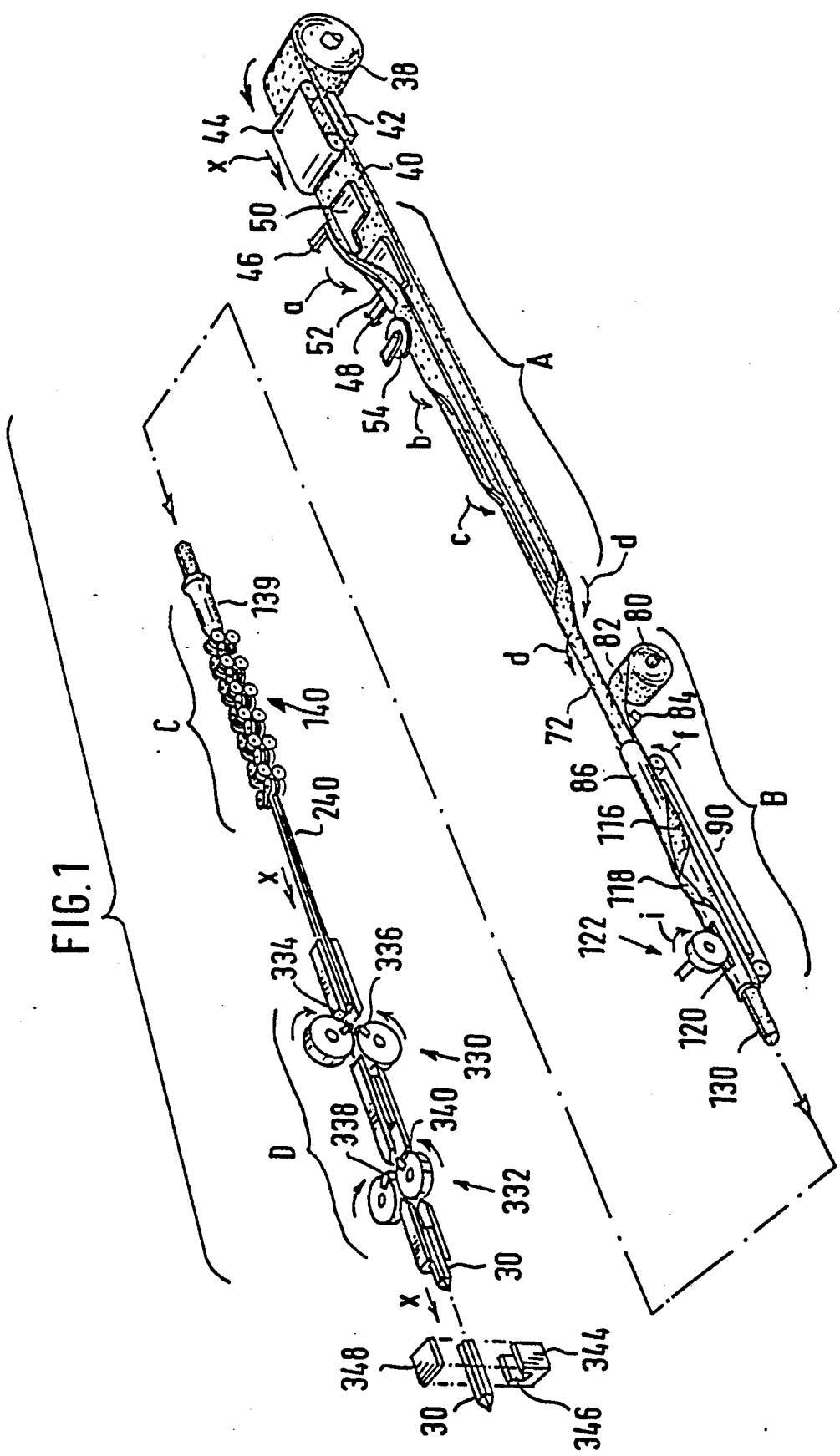
FIG. 1 shows a partially diagrammatic perspective view of the apparatus according to the invention with folding, sheathing-band application, press and severing stations.

FIG. 1 illustrates an apparatus for the continuous production of absorbent bodies 30, in this particular case of tampons 32 for feminine hygiene (FIG. 19), which are equipped at their front end with a round dome 35, on the circumference with four longitudinal grooves 31 and at their rear end 34 with a depression 33 and with a recovery band 36, the ends of which are connected by means of a knot 37.

According to FIG. 1, the apparatus consists of a stock roll 38 for a web of fibre material 40 which is processed continuously in successively arranged stations, namely a folding station A, a sheathing-band application station B, a press station C and a severing station D.

Folding station

It is evident from FIG. 1 that a stationary guide plate 42 for the endless web of fibre material 40 is arranged behind the stock roll 38 in the direction of advance x of the web of fibre material 40 Mounted at a distance above the guide plate 42 is an endless conveyor belt 44 which is preferably vertically adjustable and which, by means of a frictional connection, ensures the continuous transport of the web of fibre material 40 in the direction of the arrow x. In contrast to the embodiment illustrated, instead of the guide plate 42 there can equally well be an endless conveyor belt, in which case at least one of the conveyor belts is drivable. These devices, like the stations described below and the devices belonging to these, are arranged on a stand, of which only stand parts 46 and 48 are indicated. Furthermore, it goes without saying that the guide plate 42 extends at least over a substantial part of the underside of the folding station A and for the sake of clarity is merely indicated in FIG. 1.

Behind the conveyor belt 44 in the direction of advance x, a lead plate 50 is arranged above the web of fibre material 40, and behind it is a folding plate 52 followed by a rotatable folding disc 54. By means of this first folding plate 52, according to FIG. 2 the longitudinal side 56 on the right in the direction of movement x undergoes a first folding operation I. In this, the longitudinal side 56 of the web of fibre material 40 on the right in the direction of movement x is folded round upwards in the direction of the arrow a in parallel with the longitudinal direction of the web of fibre material 40 and laid onto the top side of the web of fibre material 40. It is evident from FIGS. 2 and 3 that, after the folding operation I, the right longitudinal edge 58 assumes a greater distance from the left longitudinal edge 60 than the longitudinal mid-axis of the web of fibre material 40 In the present exemplary embodiment, the web of fibre material 40 has a width of 25 cm. In this instance, the width of the first fold 62 appropriately amounts to 9 cm. The dimensions of the web of fibre material 40 can differ according to the intended use of the particular absorbent bodies produced As a rule, however, the width of the web of fibre material 40 will be in the range between 15 and 40 cm.

Figure 2:
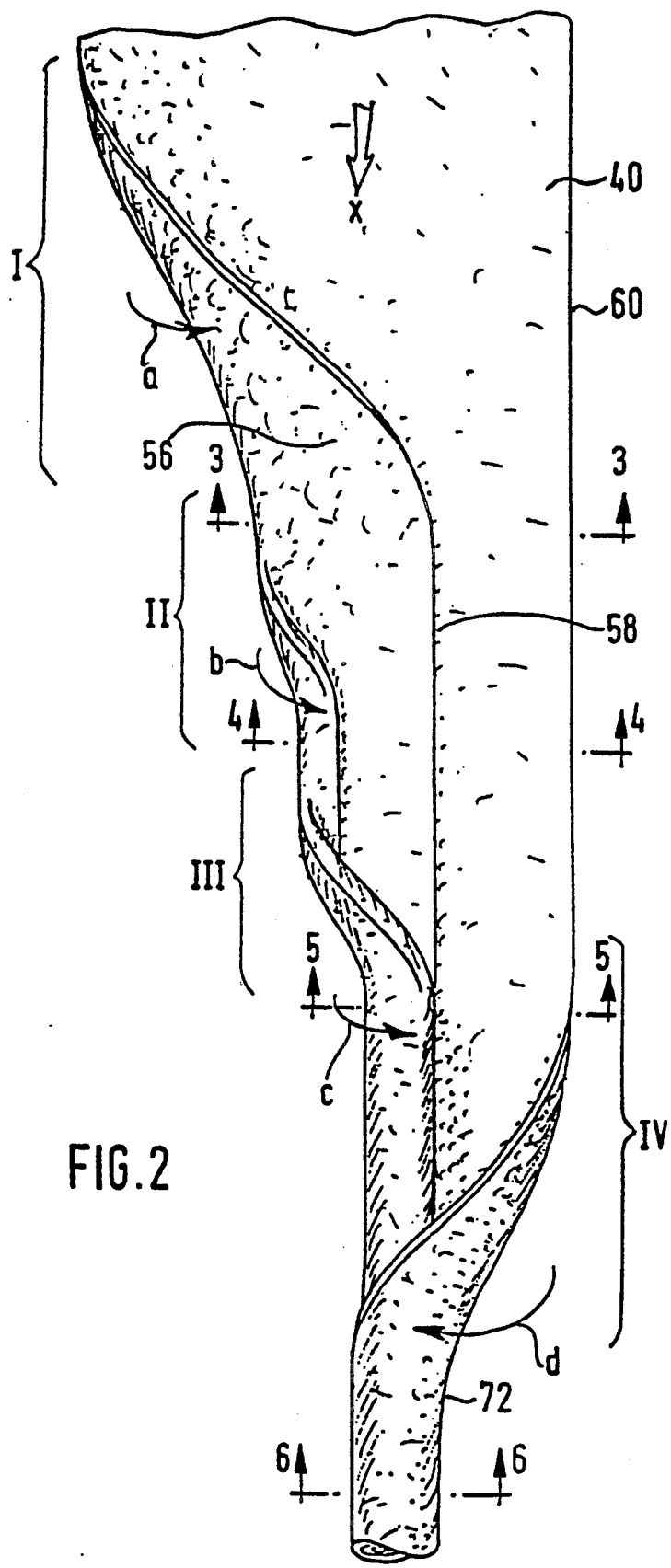
FIG. 2 shows a top view of the folding pattern of the web of fibre material.
Figure 3:
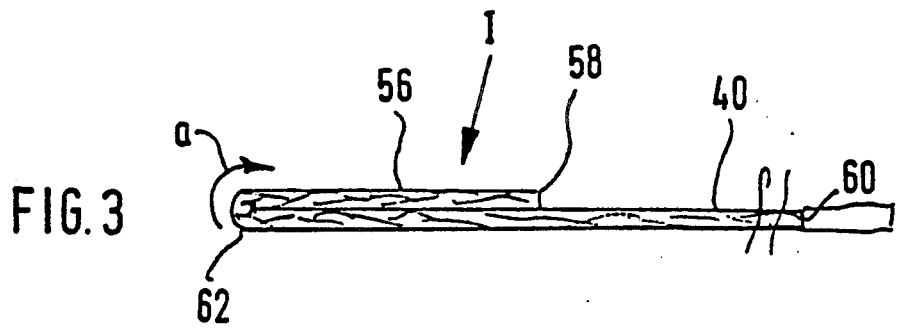
FIG. 3 shows a cross-section along the line 3—3 of FIG. 2, showing the first folding of the web of fibre material.
Figure 4:
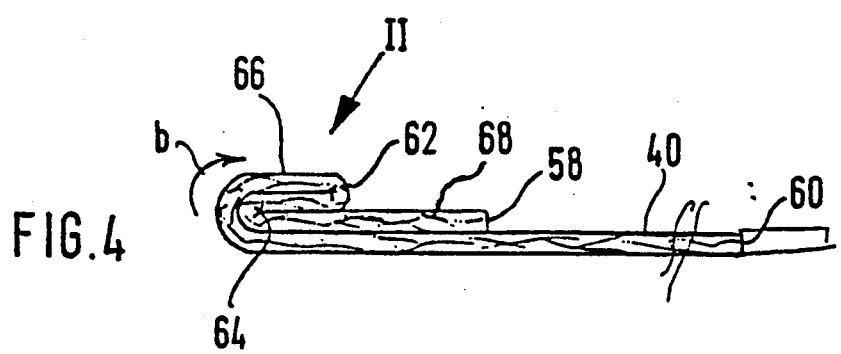
FIG. 4 shows a cross-section along the line 4—4 of FIG. 2, showing the second folding of the web of fibre material.

It is clear from further reference to FIGS. 1, 2 and 4 that the first folding operation I is followed by a second folding operation II which is once again carried out by means of suitable folding plates and folding rollers, although these are not shown in detail for the sake of clarity in the drawing. This folding operation II involves folding the right longitudinal edge formed by the fold 62 in the direction of the arrow b onto the folded-round right longitudinal side 56 about a longitudinal fold 64 and onto the top side of the longitudinal side 56 and laying it down approximately over the middle third of the width of the longitudinal side 56. This second folding takes place over a width of approximately 2 cm in the case of the abovementioned width of the web of fibre material 40.

Figure 5:
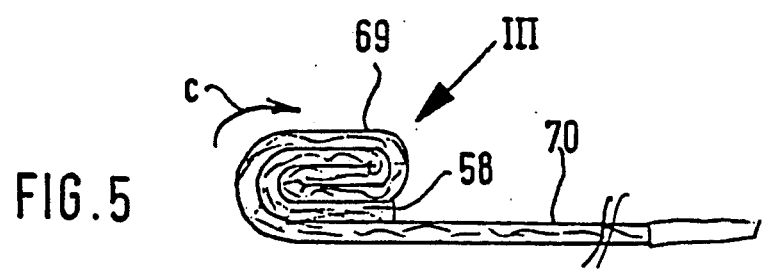
FIG. 5 shows a cross-section along the line 5—5 of FIG. 2, showing the third folding of the web of fibre material.

As is evident from FIGS. 1, 2, 4 and 5, there follows a folding operation III, in which the four-layered stack 66 is folded round in the direction of the arrow c onto the still uncovered part 68 of the right longitudinal side 56 on the left according to FIG. 5, as seen in the direction of movement x of the web of fibre material 40, so that the web of fibre material 40 is now limited in the direction of movement on its right side by a six-layered stack 69. This folding operation III extends over approximately 3.5 cm in the case of the abovementioned width of the web of fibre material 40.

Figure 6:
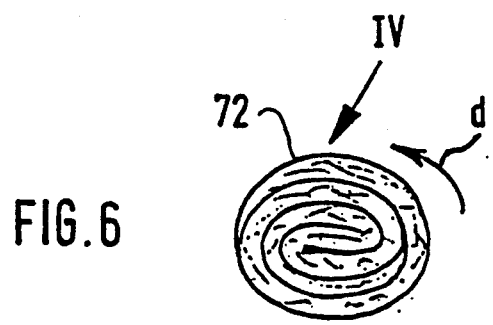
FIG. 6 shows a cross-section along the line 6—6 of FIG. 2, showing the folded web of fibre material after a side edge has been laid round onto the top side of the folded part of the web of fibre material.

The left longitudinal side 70 of the web of fibre material 40 still remaining according to FIG. 5 is now laid, as seen in the direction of movement x of the web of fibre material 40, in the opposite direction according to the arrow d in FIGS. 1, 2 and 6 round the left edge of the six-layered stack 69 and onto its top side, thereby forming as a result of this folding operation IV a seven-layered web of fibre material 72 which is completely surrounded by the remaining left longitudinal side 70 of the web of fibre material 40. At the end of the folding station A there are profile rollers which give the seven-layered web of fibre material 72 the round cross-section according to FIG. 6. Press rollers of this type are known and are therefore not shown. The left longitudinal side 70 of the web of fibre material 40 has a width of approximately 6 cm before the execution of the folding operation IV. Of course, another method of longitudinal folding or layering of the web of fibre material 40 can also be carried out according to the particular intended use of the absorbent body.

Sheathing-band application station

It can be seen from FIG. 1 that the sheathing-band application station B has a stock roll 80 for a sheathing band 82 in the region of the completely layered and rounded web of fibre material 72 The sheathing band 82 is permeable to liquid, the fibre material of the sheathing band preferably having a water-repellant finish and containing at least partially thermoplastic constituents. Advantageously, the sheathing band 82 consists of a nonwoven fibre layer having thermoplastic constituents. This sheathing band 82 is made wider than the circumference of the web of fibre material 72. A lead roller 84 is arranged transversely relative to the direction of movement x behind the stock roll 80 at a short distance below the web of fibre material 72 According to FIG. 7, the function of this lead roller 84 is to guide the sheathing band 82, fed in the direction of the arrow d from the stock roll 80, in the direction of the arrow e under a guide tube 86 and into a direction parallel to the web of fibre material 72.

The guide tube 86 is arranged downstream of the lead roller 84 for the web of fibre material 72. Its purpose is to maintain the round cross-section of the web of fibre material 72. The inner wall of the guide tube 86 is accordingly of essentially circular-cylindrical form.

Figure 7:
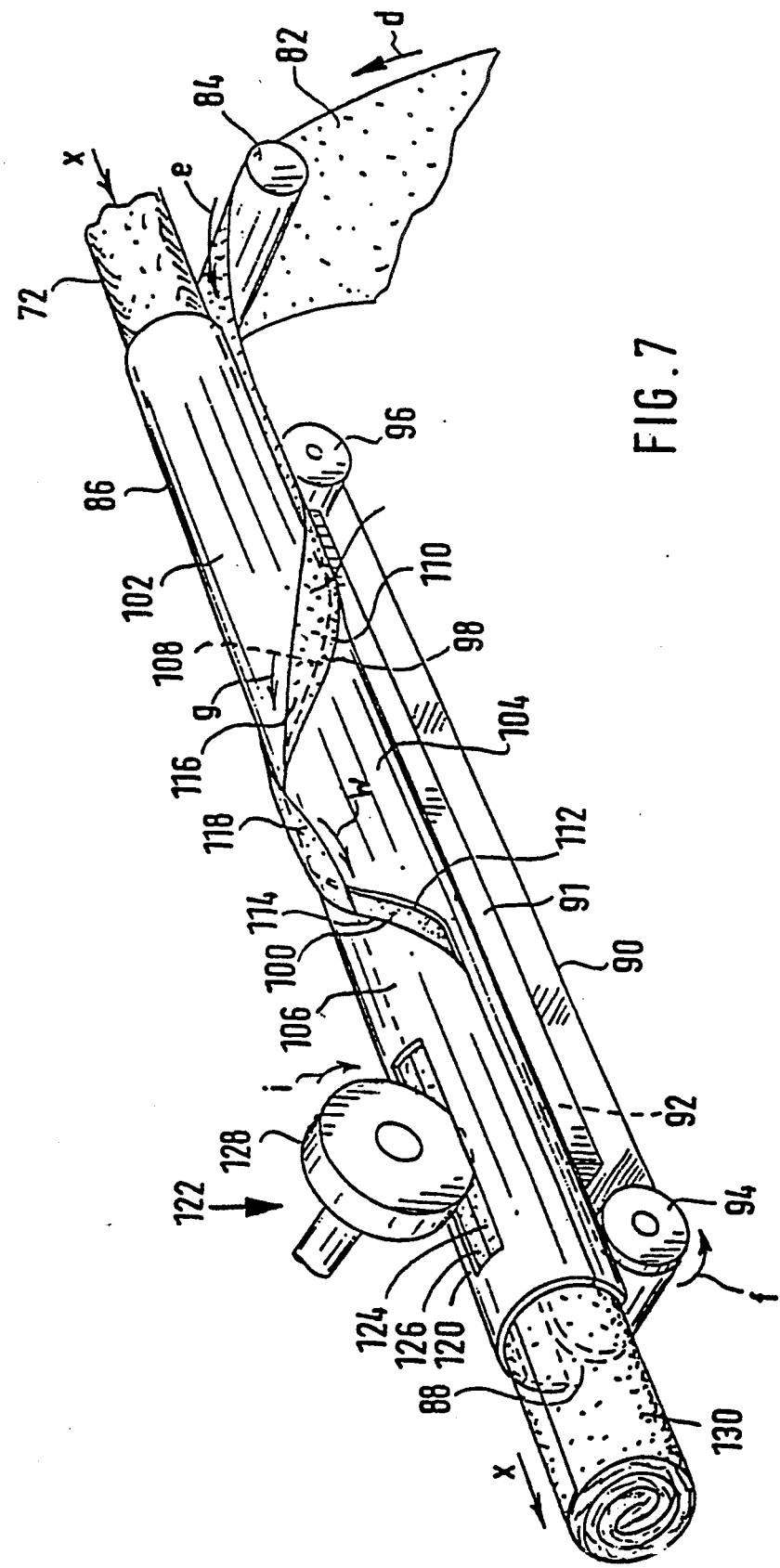
FIG. 7 shows a perspective front view of the sheathing-band application station.

On the underside, the guide tube 86 is equipped with a longitudinal slot 88 which can be seen in FIG. 7. Arranged on the underside of the guide tube 86 is an endless conveyor belt 90 which is made narrower than the longitudinal slot 88. It is thereby possible to guide the upper strand 92 of the conveyor belt 90 in the region of the longitudinal slot 88 of the guide tube 86 by means of a support plate 91, in such a way that the web of fibre material 72 is taken up as a result of a frictional connection. The endless conveyor belt 90 is guided in the conventional way round a driving roller 94 and a deflecting roller 96 and is driven in the direction of the arrow f, so that the upper strand 92 can be driven in the direction of movement x of the web of fibre material 72 at a speed which corresponds to the conveying speed of the web of fibre material 72.

The sheathing band 82 is guided by means of the lead roller 84 between the top side of the upper strand 92 of the conveyor belt 90 and the underside of the web of fibre material 72 in the region of the longitudinal slot 88 and is taken up as a result of the frictional connection occurring thereby between the upper strand 92 and the web of fibre material 72.

The guide tube 86 is equipped on the left and right sides in the direction of movement x of the web of fibre material 72 with respective introduction slots 98, 100 which are formed by successively arranged segments 102, 104 and 106 of the guide tube 86. It is evident that the two introduction slots 98, 100 are offset in the axial direction of the guide tube 86. At the same time, the segment 104 is formed in a twisted manner, in such a way that the trailing edge 108 of the first segment 102 forming an acute angle with the core of the guide tube 86 and extending similarly to a helix assumes a shorter radial distance from the tube core than the leading edge 110 of the segment 104 likewise limiting the introduction slot 98.

In a similar way, the radius of that edge 112 of the segment 104 located at the rear in the direction of movement x is made smaller than the radius of the leading edge 114 of the rear segment 106 of the guide tube 86 likewise limiting the right introduction slot 100.

For the sake of clarity in the drawing, FIG. 7 does not show the sheathing band 82 in its full width which ensures that the sheathing band has left and right side tabs 116, 118 which are laid round the guide tube 86 upwardly by guide rollers known per se and therefore not shown and which slide along on this. However, FIG. 7 shows the left side tab 116 of the sheathing band 82, as it is being introduced into the left introduction slot 98 beyond the outer surface of the segment 102 in the direction of the arrow g and laid by means of the segment 104 onto the rounded, essentially cylindrical, surface of the web of fibre material 72. Similarly, the right side tab 118 of the sheathing band 82 is subsequently likewise laid in the direction of the arrow h over the outer face of the segment 104, through the right introduction slot 100 and onto the surface of the rounded web of fibre material 72 by means of the segment 106. At the same time, the outer longitudinal edge 124 of the right side tab 118 overlaps that longitudinal edge 126 of the left-side tab 116 of the sheathing band 82 first laid onto the top side of the web of fibre 72.

FIG. 7 also shows that the guide tube 86, in the region of the rear segment 106, is likewise equipped on the top side with a middle longitudinal slot 120 for a closing device 122 which serves for connecting together the longitudinal edges 124, 126 of the side tabs 116, 118 of the sheathing band 82. In the present exemplary embodiment, the closing device 122 consists of a hot-sealing roller 128 which is made narrower than the longitudinal slot 120 and which consequently bears through the longitudinal slot on the mutually overlapping edges 124, 126 and seals these to one another as a result of the softening of thermoplastic constituents of the sheathing band 82. The hot-sealing roller 128 can be heated in a way known per se by means of electrical resistance heating and can be driven in the direction of rotation of the arrow i at the conveying speed of the rounded sheathed web of fibre material 130 which leaves the guide tube 86 at its end.

Press station

Figure 8:
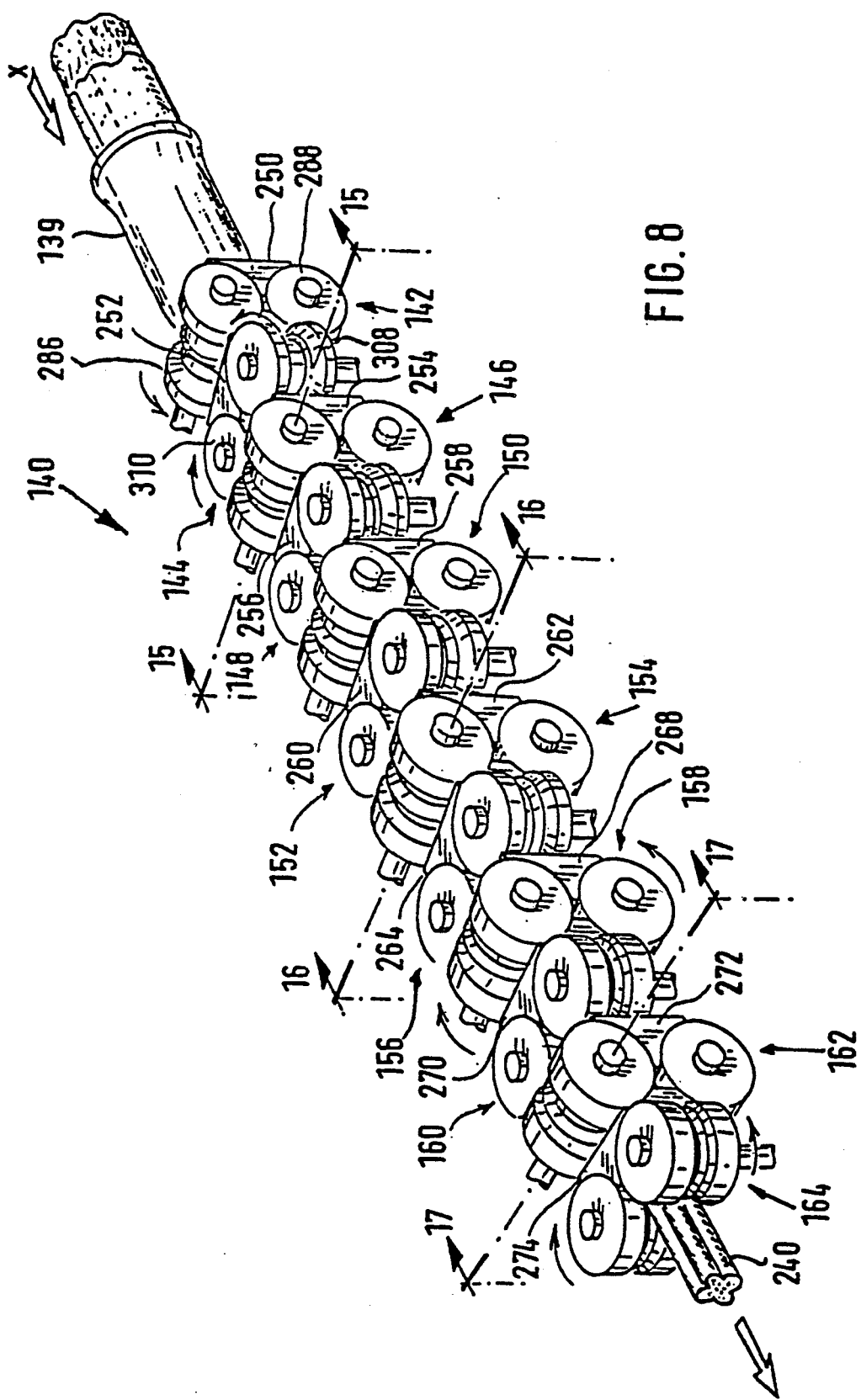
FIG. 8 shows a perspective front view of the press station.
Figure 13:
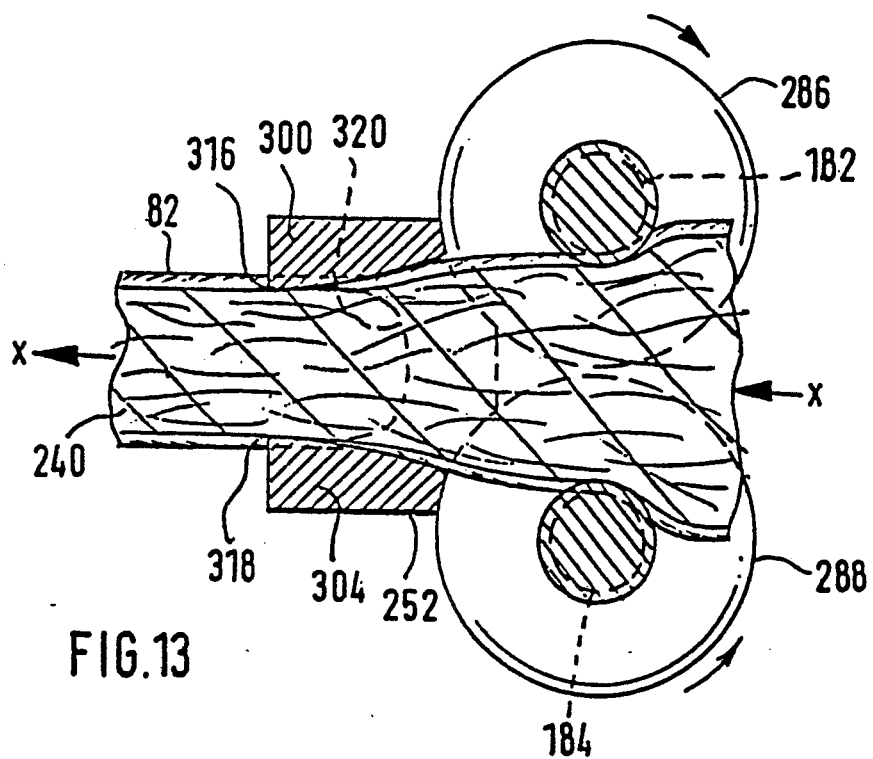
FIG. 13 shows a cross-section along the line 13—13 of FIG. 10.

Referring to FIGS. 1 and 8, the press station C consists of a feed tube 139 and of a roller frame 140 composed of a plurality of oppositely drivable pairs of rollers 142, 144, 146, 148, 150, 152, 154, 156, 158, 160, 162, and 164. As shown in FIGS. 1 and 8, the pairs of rollers are successively arranged respectively offset relative to one another at 90°. The pairs of rollers 142, 146, 150, 154, 158 and 162 are respectively arranged in a vertical plane horizontally and in parallel above one another In contrast, the pairs of rollers 144, 148, 152, 156, 160 and 164 are respectively aligned vertically and parallel to one another in vertical planes. There is the least possible distance between the said successive pairs of rollers.

The roller frame 140 is composed of three groups of pairs of rollers which differ from one another in that the nip of the first group of pairs of press rollers 142, 144, 146, and 148 which is formed by the free rolling cross-section is reduced successively in steps more pronouncedly than the nip of the following second group of pairs of press rollers 150, 152, 154 and 156 which is formed by the free rolling cross-section. The third group is formed by pairs of smoothing rollers 158, 160, 162 and 164 which each have the same nip size. It is clear that, for example, both the number and the circumference of the groups of rollers can be changed according to the type of absorption body to be produced.

Figure 15:
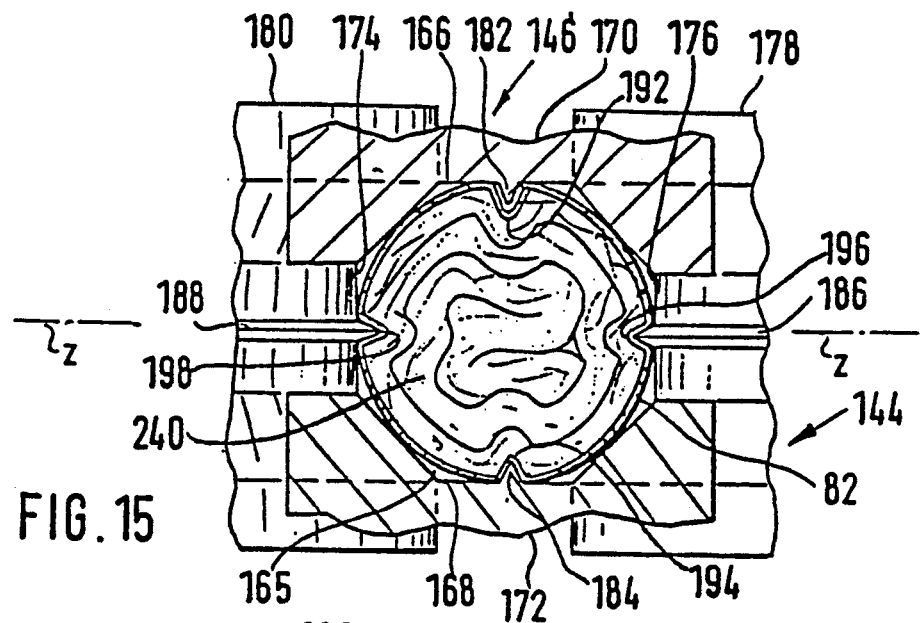
FIG. 15 shows a cross-section along the line 15—15 of FIG. 8.

FIG. 15 illustrates in a partially cutaway representation a cross-section through the horizontally arranged pair of press rollers 146, in front of which in the upstream direction the pair of press rollers 144 offset at 90° and rotatable about vertical shafts can be seen. It is evident that the roller profiles 166, 168, symmetrical relative to the bisecting plane z—z of the nip 165, of the upper roller 170 and of the lower roller 172 of the pair of press rollers 146 are made in the form of a three-centre curve and, together with a profile bottom 174, 176 of the vertical roller 178, on the left in the conveying direction x, and of the right vertical roller 180 of the pair of press rollers 144, form a free rolling cross-section which corresponds to an equilateral octagon symmetrical relative to the bisecting plane z—z of the nip 165 of the rollers 170, 172. Because the pairs of press rollers 144 and 146 shown in FIG. 15 are arranged in direct succession in the conveying direction x, first the rollers 178, 180 of the vertical pair of press rollers 144 continuously act diametrically on the web of fibre material in the horizontal direction, in order to roll from the latter a fleece rod 240, the cross-section of which is likewise shown in FIG. 15. Subsequently, the fleece rod 240 is subjected diametrically in the vertical direction to a rolling pressure by means of the rollers 170, 172 of the horizontal pair of press rollers 146. Because the successive pairs of press rollers are arranged offset at 90°, this prevents the formation of a longitudinal rolling burr on the fleece rod 240 and at the same time reduces the cross-section of the latter in steps in each case.

As also emerges from FIG. 15, the mutually-parallel profile bottoms 166, 168 of the horizontal pair of press rollers 146 and the profile bottoms 174, 176 of the vertical pair of press rollers 144 are each equipped in the centre with a circumferential rib 182, 184 and 186, 188. The profile of the circumferential ribs is triangular and tapers outwards. If appropriate, however, the circumferential rollers can also have a different profile, for example an angular or round profile. The circumferential ribs of each pair of press rollers have the same dimensions, so that the fleece rod 190 sheathed in the sheathing band 82 can be equipped with corresponding approximately V-shaped longitudinal grooves 192, 194 and 196, 198 at locations on its circumference which are offset at 90°.

Figure 16:
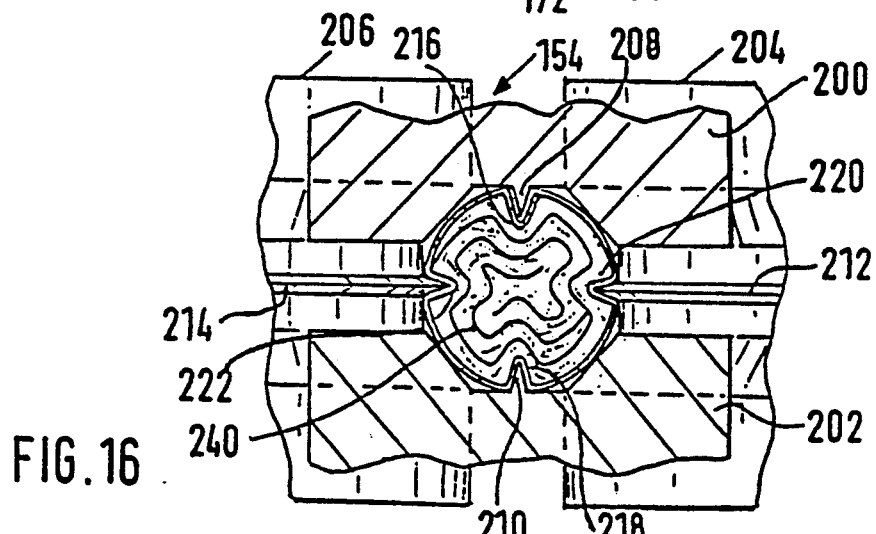
FIG. 16 shows a cross-section along the line 16—16 of FIG. 8.

FIG. 16 shows the pair of press rollers 154 with the horizontal upper roller 200 and the lower roller 202 located at a distance below it and in parallel in a vertical plane. The vertical rollers 204 and 206 of the pair of press rollers 152 preceding it in the conveying direction x of the fleece rod 190 can be seen. It is evident from. FIG. 16 that the free rolling cross-section formed by the two successive pairs of rollers 152 and 154 corresponds once again to an approximately equilateral octagon. However, this free octagonal rolling cross-section is made substantially smaller in comparison with that described with reference to FIG. 15. Furthermore, FIG. 16 shows that, for the further deepening of the longitudinal grooves 192, 194, 196 and 198 of FIG. 15, the circumferential ribs 208, 210 of the upper roller 200 and of the lower roller 202 and the circumferential ribs 212 and 214 of the preceding vertical rollers 204, 206 have a foot of approximately equal width. However, the circumferential ribs 212, 214, with their profile likewise tapering outwards, project so far radially outwards beyond mid-height of the profile depth of each roller in the mid-plane of the profile of the latter that sharply pronounced V-shaped longitudinal grooves 216, 218, 220 and 222 can be formed in the fleece rod 240 of now greatly compressed cross-section and in its sheathing band 82.

A smaller reduction of the cross-section of the fleece rod 240 takes place in the second group formed by the pairs of press rollers 150, 152, 154 and 156. In the present exemplary embodiment, this reduction amounts in each case to approximately 0.5 mm in the second group of press rollers in comparison with 1 mm in the first group. The fleece rod 240 is thereby compressed to an even smaller cross-section which has been reduced to the final cross-section of the fleece rod 240 shown in FIG. 17 by means of the preceding pair of press rollers 156 with the roller 224, on the left in the conveying direction x, and the right roller 226 of the vertical pair of press rollers 160 of the second group.

The horizontal upper roller 228 and lower roller 230 of the pair of rollers 162, like the following pair of rollers 164, are designed as smoothing or calibrating rollers, of which the nip is constant and serves for stabilizing the form or cross-section of the fleece rod 240 and smoothing the surface of the latter.

Figure 17:
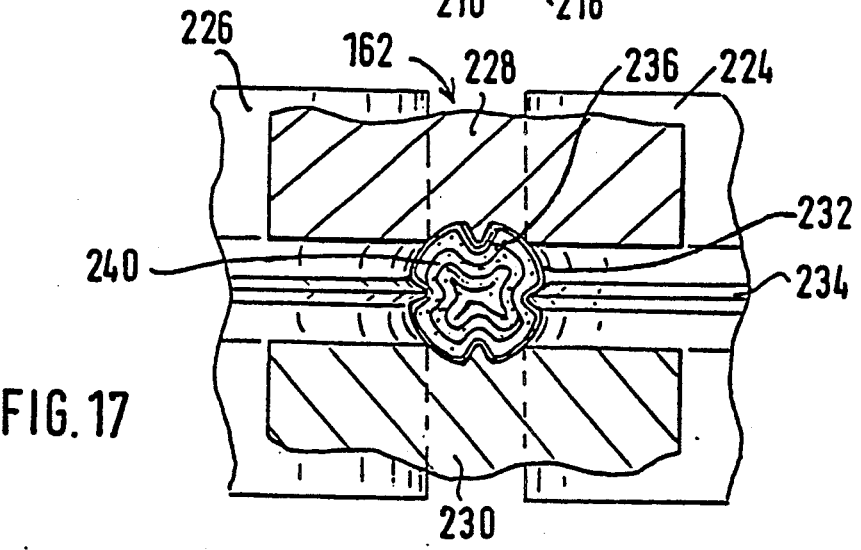
FIG. 17 shows a cross-section along the line 17—17 of FIG. 8.

The profile of the pairs of smoothing rollers 228, 230 and 224, 226 in FIG. 17 differs from the profile shown in FIGS. 15 and 16 by having a basic form 232 essentially in the form of an arc of a circle. The middle circumferential rib 234 of tapered profile of all four rollers mentioned projects radially to approximately the height of the cylindrical diameter of these rollers. For the sake of simplicity, in this particular case all the circumferential ribs of the said smoothing rollers are given the reference symbol 234 in FIG. 17. By means of the nip described, the fleece rod 240 acquires a cross-sectional form, in which pronounced longitudinal grooves 236 lying diametrically opposite one another in pairs and arranged at equal angular intervals of 90° are formed in the fleece rod 240 by the circumferential ribs 234. Here too, for the sake of simplicity, the longitudinal grooves 236 of the fleece rod 240 are given only the single reference symbol 236. In contrast to the exemplary embodiment described and according to the particular intended use of the absorbent bodies, it is possible to produce the fleece rod 240 without longitudinal grooves or to equip it with a larger number of longitudinal grooves which should preferably always be distributed uniformly over the circumference of the fleece rod 240. Where the production of tampons is concerned, the arrangement of longitudinal grooves is advantageous because it leads to a partial compression of the fibre material in the longitudinal mid-axis of the fleece rod 240, this resulting in a stability or buckling resistance of the finished tampon which exceeds the stability and buckling resistance of known tampons. It can be assumed that this advantage is related to the continuous stepped press-rolling of the fleece rod 240 in the roller frame 140 described.

The horizontal pairs of smoothing rollers 158, 162 in FIG. 8 are followed by the vertically arranged pairs of smoothing rollers 160, 164 with the same nip as the pair of smoothing rollers 158, so that the fleece rod 240 is smoothed over its entire circumference and its cross-sectional form stabilized.

A control device known per se and therefore not shown serves for maintaining the same mean circumferential speed of all the press and smoothing rollers arranged in the roller frame 140.

The shaping and stabilization of the form of the fleece rod can be assisted, if appropriate, by preferably equipping the cylindrical circumferential portions of the roller profiles with a rubber or plastic coating, in order to increase the friction relative to the fleece rod.

Furthermore, where appropriate, some or all of the pairs of press and/or smoothing rollers can be heated, so that the shaping of the fleece rod 240 is accompanied by a certain ironing effect which increases the dimensional stability of the fleece rod. At the same time, the nip of the successively arranged pairs of press rollers of the first and second group can be calculated so that the fleece rod 240 is rolled down only approximately to the final cross-section of the desired absorbent body. However, at least where the production of tampons for feminine hygiene is concerned, it is recommended that the fleece rod 240 be rolled down considerably beyond the final cross-section of the tampon to a smaller cross-section, because the fibres of the fleece rod have a natural elasticity which causes the cross-section of the finish-pressed tampon to expand Consequently, it is possible to calculate the reduction of the final cross-section of the fleece rod in such a way that the tampon, after it has been finished, expands to a final cross-section which corresponds to the physiological preconditions for its use.

Moreover, it can be seen from FIG. 8 that guides in the form of guide surrounds 250, 252, 254, 256, 258, 260, 262, 264, 266, 268, 270, 272 and 274 fill essentially completely the interspaces between the successive pairs of press and smoothing rollers 142 to 164 for the positive guidance of the fleece rod 240. In accordance with the 90° offset of the successive pairs of press and smoothing rollers, the said guide surrounds 250 to 274 are also successively arranged offset respectively at 90° relative to one another in the conveying direction x of the fleece rod 240. To allow this positive guidance of the fleece rod 240 within the roller frame 140, the clear entry cross-section of each guide surround is made smaller than the nip of the pair of press rollers preceding the guide surround, whilst the clear cross-section of the exit end of each guide surround is larger than the nip of the pair of press rollers following the guide surround.

Referring to FIGS. 9 and 12, the clear cross-section of the guide surrounds is essentially elliptic or oval. At the same time, the major axis 278 of the elliptic or oval cross-section of each guide surround between successive pairs of press rollers 142 to 160 is arranged parallel to the major axis of the particular pair of press rollers 142 to 162 preceding in relation to the conveying direction x of the fleece rod 240. Thus, the diametrical pressing of the fleece rod 240 by the pair of press rollers preceding each guide surround takes place in each case in the direction of the minor axis 280 of the essentially elliptic or oval cross-section of each guide surround (FIG. 12). The cross-section of the fleece rod 240 is at the same time shaped into an elliptic or oval form. The fleece rod 240 coming out of the respective pair of press rollers is received positively by the corresponding cross-section of each guide surround, the said cross-section narrowing in the conveying direction of the arrow x. The fleece rod 240 is fed to the following pair of press rollers by a guide surround narrowing towards its rear end so as to leave a cross-section which assists or prepares the reduction of the cross-section of the fleece rod by the following pair of rollers.

This cross-sectional reduction towards the rear or outlet end which is ensured at each guide surround is evident above all from FIGS. 9, 11, 12, 13 and 14. FIG. 9 shows the guide surround 252 of those guide surrounds 252, 256, 260, 264 and 270 which are arranged respectively between a preceding horizontal pair of press rollers 142, 146, 150, 154, 158 and a vertical pair of press rollers 144, 148, 152, 156, 160 located behind the guide surround. The guide surround 252 in FIG. 9 is arranged behind the pair of press rollers 142 represented by dot- and dash-lines and in front of the following vertical pair of press rollers 144, as seen in the conveying direction of the fleece rod (not shown) indicated by the arrow x and fills the interspace between these two pairs of press rollers essentially completely The front side is equipped with flanks 282, 284 which correspond to the horizontal pair of press rollers 142 and are in the form of a cylinder cutout and converge in a funnel-shaped manner and into which the upper and lower rollers 286, 288 engage rotatably. Two lateral jaws 290 and 292 project into the interspace formed by the upper roller 286 and the lower roller 288 of the horizontal pair of press rollers 142 and thereby extend the conical guide face 294 of the guide surround 252. The conically narrowing guide face 294 is continued in the conveying direction of the arrow x by a tapering upper guide rib 296 and a lower, identically tapering guide rib 298 which are limited laterally by the flanks 300, 302 and 304, 306 tapering in a funnel-shaped manner. These flanks are matched to the circumferential faces of the vertical rollers 308, 310 of the pair of press rollers 144, the front ends 312, 314 of the guide ribs 296, 298 coming close to the narrowest point of the nip of these vertical rollers 308, 310.

For clarification, FIGS. 11, 12, 13 and 14 show on an exaggerated scale the reduction of the clear cross-section 276 of the guide surround 252 in the direction of the minor axis 280 of the essentially elliptical or oval cross-section of the guide surround The U-shaped cross-section 320 formed by the lateral jaws 290, 292 and the guide ribs 296, 298, open in the direction of the arrow x in FIG. 11 and intended for the roller profiles of the vertical press rollers 308, 310, narrows forwards, so that the inner front corners 316, 318 of the guide ribs 296, 298, limiting the elliptic guide face 294 tapering in a nozzle-like manner are arranged at a smaller distance from one another than a length portion 322, 324 of the guide ribs 296, 298 which is located behind them.

Figure 14:
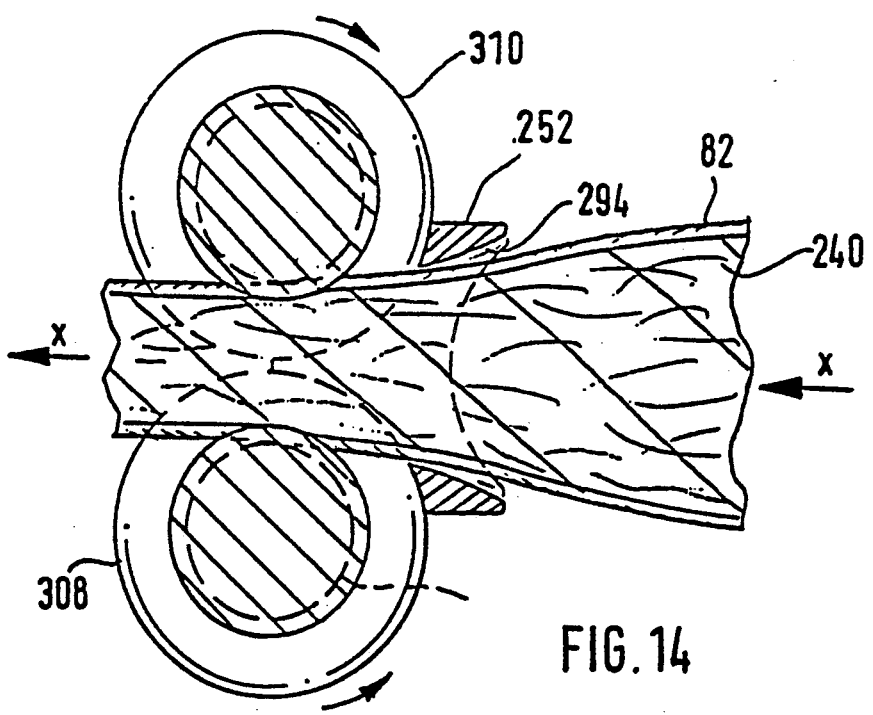
FIG. 14 shows a cross-section along the line 14—14 of FIG. 11.

Consequently, the inner front corners 314, 316 engage into the upper and lower longitudinal groove 192, 194 of the fleece rod 240 (FIG. 15) and thereby form an axial guide for the fleece rod 240. However, the longitudinal grooves of the fleece rod 240 which are shown in FIGS. 15 to 17 are not a precondition for this shape of the guide surrounds. On the contrary, this shape of the guide surrounds serves for positively guiding and compacting the fleece rod 240 in that diametrical direction extending perpendicularly relative to the pressing direction, to which the fleece rod 240 is exposed by the following vertical pair of press rollers 144, namely in the horizontal direction of the major axis 278 of the elliptical cross-section of the guide surround 252 in FIG. 12. The guide ribs 296, 298 of the guide surround 252 in FIG. 9 therefore each exert the particular radial pressing force on the fleece rod 240. Moreover, this applies, albeit to a smaller extent, to the guide face 294 in the region of the lateral jaws 290, 292. At the same time, the guide face 294 widens conically in the region of the entry cross-section, to such an extent that the fleece rod 240 can easily be moved into the guide surround 252, as can be seen in FIG. 14. It is therefore clear that an essentially complete positive guidance of the fleece rod 240, allowing an unimpeded conveyance of the fleece rod through the roller frame 140, is guaranteed over the entire length of the roller frame 140.

Severing station

The severing station D in FIG. 1 consists of at least two mutually oppositely drivable pairs of pinching rollers 330, 332, which are offset at 90° and of which the first pair of pinching rollers 330 is arranged superposed horizontally and in parallel in a plane perpendicular relative to the direction of advance x, whilst the second pair of pinching rollers 332 is arranged vertically at a distance and mutually parallel in a plane perpendicular relative to the direction of advance The pinching rollers of the two pairs of pinching rollers 330, 332 are each equipped with a pinching projection 334, 336 and 338, 340. The pinching projections 334, 336 reduce the cross-section between successive length portions of the fleece rod 240 corresponding approximately to the length of the tampon 32, with the exception of a thin axial connecting web (not shown). This connecting web is severed by the last pair of pinching rollers 332 of the severing station D, and, as a result of the relatively high circumferential speed of the pinching rollers 338, 340 corresponding to the conveying speed of the fleece rod 240, is ejected with relatively sharp axial impetus. While the absorbent body 30 is being pinched by the pairs of pinching rollers 330, 332, at the same time the front end 342 of the absorbent body 30 is preformed pyramidally, as can be seen from FIG. 20. In contrast, the rear end face of the absorbent body 30 already has a pyramidal recess.

When a sheathing band 82 is used, it is recommended that at least one pair of cutting rollers as a cutting device be arranged at the end and/or at the start of the severing station D, so that the sheathing band 82 surrounding the fleece rod 240 and/or the thin axial connecting web between successive portions of the fleece rod 240 can be severed. The cutting rollers are not shown because they are generally known in the art.

FIGS. 1 and 20 show that the absorbent body 30, after being severed, is transferred into a take-up means 344 which is made narrower than the length of the absorbent body 30. For receiving the absorbent body 30, the take-up means 344 is equipped with a U-shaped transverse indentation 346 which is closed at the top by means of a take-up means lid 348 after the absorbent body 30 has been received. A plurality of take-up means 344 of this type are fastened to the outside of a endless conveying member 350 movable continuously in the direction of the arrow n and represented merely by dot- and dash- lines in FIG. 20, so that the take-up means 344 can continuously receive the absorbent bodies 30 ejected from the severing station D. The means for transferring the absorbent bodies into the take-up means belong to the state of the art and are therefore not shown.

FIG. 20 shows that, in parallel with the plane of movement of the endless conveying member 350, on both sides further endless conveying members 352 and 354 are arranged on each side of the conveying member 350.

The conveying member 352 carries a plurality of domeforming devices 356 which are move synchronously with the take-up means 344 in the direction of the arrow n. According to FIG. 20, each of the domeforming devices 356 consists of a U-shaped part 358, the legs 360, 362 of which are directed parallel to the plane of rotation of the endless conveying member 352. These legs 360, 362 are equipped with coaxial bores 364, 366, through which a rod 368 is guided. That end of the rod 368 projecting from the leg 362 in the direction of the take-up means 346 carries a forming die 370 which is equipped with a recess 372 in the form of a round dome. The recess 372 has a larger diameter than the absorbent body. If appropriate, this forming die 370 can be heated, for example by means of electrical resistance heating.

The end of the rod 368 projecting from the leg 360 of the U-shaped part 358 on the side facing away from the leg 362 carries a sensing roller 374. Into the path of movement of this sensing roller 374 extends a stationary control cam 376 with a control surface 378 which the sensing roller 374 meets. Since a helical compression spring 380 is supported between the outer face of the leg 360 of the U-shaped part 358 and the sensing roller 374, the sensing roller 374 together with the rod 368 and the forming die 370 is always prestressed in the direction of the control surface 378. Since the control cam 376 extends increasingly into the path of movement of the sensing roller 374 in the direction of movement of the conveying member 352 indicated by the arrow n, the forming die 370 is moved axially up against the preformed front end 342 of the absorbent body 30, because the take-up means 344 and the U-shaped part 358 rotate coaxially and in synchronism. Consequently, the preformed front end 342 is shaped into a round dome 35, as shown by the tampon 32 in FIG. 19. The direction of movement of the sensing roller 374 is represented by a broken arrow s. The axial stroke of the rod 368 is limited by a stop disc 382 which is fastened to that length portion of the rod 368 located between the legs 360, 362 and which normally bears against the inner face of the leg 360 under the effect of the helical compression spring 380.

The endless conveying member 354 is arranged on that side of the take-up member 350 located opposite the conveying member 352 for the forming die 372, at a distance and parallel to the take-up means conveying member 350 and is movable in synchronism with the latter. The conveying member 354 is equipped with a number of embossing devices 384 corresponding to the number of forming devices 356. These embossing devices 384 likewise consist of a U-shaped part 386, the mutually parallel legs 388, 390 of which are once again equipped with axial bores (not shown) through which is guided a rod 392 equipped, on the outer face of the leg 388 facing the take-up means 386, with an embossing head 394, the end face of which is equipped with a convex spherical cup 396. On the outside of the conveying member 354 is arranged once again a control cam 398 with a control surface 400 which extends into the path of movement of a sensing roller 402. Between the sensing roller 402 at the lower end of the rod 392 and the leg of the U-shaped part 386, a helical compression spring 404 is arranged on the rod 392. A stop disc 404 is fastened to that part of the rod 392 extending between the legs 388, 390. The longitudinal mid-axis of the rod 392 and of the embossing head 394 is aligned coaxially with the longitudinal mid-axis of the transverse indentation 346 of the take-up means 344 and of the forming die 370. Moreover, since the control cams 376 and 398 are located opposite one another and their control surfaces 378 and 400 are of similar design, the shaping of the front end 342 of the absorbent body 30 into the form of a round dome is accompanied by a shaping of the rear end face 343 of the absorbent body 30 by the spherical cup 396 of the embossing head 394, when the sensing roller 402 meets the control surface 400, presses the embossing head 394 in the direction of the broken arrow o against the rear end face 344 of the absorbent body 30 and forms in the latter a depression 33 which, after the tampon has been finished, constitutes an insertion aid for the tampon.

Process

The essential steps in the processing of the web of fibre material 40 are summarised once again below.

Referring to FIGS. 1 to 6, in the folding station A the web of fibre material 40 is subjected to three longitudinal folding operations I, II and III from the right longitudinal side 56 and is thereby folded on itself, before the left longitudinal side 70 is laid round the web of fibre material in the opposite direction, thus producing a seven-layered web of fibre material 72. Profile rollers (not shown) round off the cross-section of the layered web of fibre material.

Subsequently, the web of fibre material 72 is introduced into the guide tube 86 of the sheathing-band application station B and is surrounded by the sheathing band 82, the longitudinal edges 124, 126 of which are scaled to one another. The web of fibre material 130 of round cross-section, surrounded by the sheathing band 82, comes out of the guide tube 86 and is thereafter fed to the press station C. In the roller frame 140 of the press station C, the web of fibre material 130 is rolled down in steps at least to the final cross-section of the absorbent body 30 and a fleece rod 240 is formed. At the same time, the rolling pressure is exerted successively in steps on diametrically opposed sides of the fleece rod 240, the pressing direction being mutually offset respectively at 90°. The fleece rod 240 is preferably rolled down to a cross-section which is made smaller than the final cross-section of the absorbent body 30, when tampons 32 for feminine hygiene are to be produced from the absorbent body. This does not preclude the possibility that, in other instances too, rolling down beyond the final cross-section of the absorbent body will be expedient. FIG. 18 shows that, during continuous rolling, the fleece rod 240 is equipped with four longitudinal grooves 31 which are located diametrically opposite one another in pairs. It is also evident that the cross-section of the fleece rod 240 is reduced first relatively sharply and then more slowly in the direction of movement x, before the outer surface of the fleece rod 240 is smoothed and calibrated at the end of the roller frame 140. It can be expedient to heat the fleece rod during press-rolling in order to increase its dimensional stability.

As explained in conjunction with FIGS. 8 to 14, during the successive pressing stages the fleece rod 240 is guided positively through the said guide surrounds 250 to 274.

The pressed fleece rod 240 is thereafter fed to the severing station D in which portions of the fleece rod 240 which correspond to the length of an absorbent body 30 are severed from one another by pinch-rolling the fleece rod diametrically and in a manner offset in steps at 90°, with the exception of an axial connecting web between the portions. At the same time, the front end of each length portion is preformed in a dome-like manner during the pinching operation. Subsequently, the individual absorbent bodies are severed in the region of the thin connecting web. The preformed dome-shaped front end of the absorbent body is thereafter shaped definitively by smoothing. At the same time, a hemispherical depression is formed in the rear end of the absorbent body, as an insertion aid for a tampon 32 according to FIG. 19 is produced from the absorbent body. Subsequently, in a way which is conventional and therefore not shown in detail, the recovery band 36, the ends of which are connected to one another, for example by means of a knot 37, is fastened to the rear end of the tampon.

| Reference Symbols | |
|---|---|
| A | Folding station |
| B | Sheathing-band application station |
| C | Press station |
| D | Severing station |
| 30 | Absorbent body |
| 31 | Longitudinal grooves |
| 32 | Tampon |
| 33 | Depression |
| 34 | Rear end |
| 35 | Round dome |
| 36 | Recovery band |
| 37 | Knot |
| 38 | Stock roll |
| 39 | Absorbent body |
| 40 | Web of fibre material |
| 42 | Guide plate |
| 44 | Endless conveyor belt |
| 46 | Stand parts |
| 48 | Stand parts |
| 50 | Guide surrounds |
| 52 | Folding plate |
| 54 | Folding disc |
| 56 | Right longitudinal side |
| 58 | Right longitudinal edge |
| 60 | Left longitudinal edge |
| 62 | First fold |
| 64 | Longitudinal fold |
| 66 | Four-layered stack |
| 68 | Uncovered part |
| 70 | Left longitudinal side |
| 72 | Seven-layered web of fibre material |
| 80 | Stock roll |
| 82 | Sheathing band |
| 84 | Lead roller |
| 86 | Guidetube |
| 88 | Longitudinal slot |
| 90 | Conveyor belt |
| 91 | Support plate |
| 92 | Upper strand |
| 94 | Driving roller |
| 96 | Deflecting roller |
| 98 | Left introduction slot |
| 100 | Right introduction slot |
| 102, 104, 106 | Segments |
| 108 | Trailing edge (Segment 102) |
| 110 | Leading edge (Segment 104) |
| 112 | Trailing edge (Segment 104) |
| 114 | Leading edge (Segment 106) |
| 116 | Left side tab |
| 118 | Right side tab |
| 120 | Longitudinal slot |
| 122 | Closing device |
| 124, 126 | Longitudinal edges |
| 128 | Hot-sealing roller |
| 130 | Rounded sheathed web of fibre material |
| 139 | Feed tube |
| 140 | Roller frame |
| 142, 144 | Pairs of rollers |
| 146, 148 | Pairs of rollers |
| 150, 152 | Pairs of rollers |
| 154, 156 | Pairs of rollers |

-continued

| Reference Symbols | |
|---|---|
| 160, 162, 164 | Pairs of rollers |
| 165 | Nip |
| 166, 168 | Roller profiles |
| 170 | Upper roller |
| 172 | Lower roller |
| 174 | Profile bottom |
| 176 | Profile bottom |
| 178 | Left vertical roller |
| 180 | Right vertical roller |
| 182, 184, 186, 188 | Circumferential rib |
| 190 | Fleece rod |
| 192, 194, 196, 198 | Longitudinal grooves |
| 200 | Upper roller |
| 202 | Lower roller |
| 204 | Vertical rollers |
| 206 | Vertical rollers |
| 208, 210, 212, 214 | Circumferential ribs |
| 216, 218, 220, 222 | Longitudinal grooves |
| 224 | Left roller |
| 226 | Right roller |
| 228 | Upper roller |
| 230 | Lower roller |
| 232 | Basic form of an arc of a circle |
| 234 | Circumferential rib |
| 240 | Fleece rod |
| 250–274 | Guide surrounds |
| 276 | Free elliptic cross-section |
| 278 | Major axis |
| 280 | Minor axis |
| 282 | Flanks |
| 284 | Flanks |
| 286 | Upper roller |
| 288 | Lower roller |
| 290 | Lateral jaws |
| 292 | Lateral jaws |
| 294 | Guide face |
| 296 | Guide rib |
| 298 | Guide rib |
| 300, 302 | Flanks |
| 304, 306 | Flanks |
| 308, 310 | Vertical press rollers |
| 312, 314 | Front ends |
| 316, 318 | Front corners |
| 320 | U-shaped cross-section |
| 322, 324 | Length portion |
| 330, 332 | Pairs of pinching rollers |
| 334, 336 | Pinching projections |
| 338, 340 | |
| 342 | Preformed front end |
| 343 | Lower end face |
| 344 | Take-up means |
| 346 | U-shaped transverse indentation |
| 348 | Take-up means lid |
| 350, 352, 354 | Endless conveying members |
| 356 | Dome-forming device |
| 358 | U-shaped part |
| 360, 362 | Legs |
| 364, 366 | Bores |
| 368 | Rod |
| 370 | Forming die |
| 372 | Recess in the form of a round dome |
| 374 | Sensing roller |
| 376 | Control cam |
| 378 | Control face |
| 380 | Helical compression spring |
| 382 | Stop disc |
| 384 | Embossing device |
| 386 | U-shaped part |
| 388 | Leg |
| 390 | Leg |
| 392 | |
| 394 | Embossing head |
| 396 | Spherical cup |
| 398, 310 | Vertical press rollers |
| 398 | Control cam |
| 400 | Control surface |
| 402 | Sensing roller |
| 404 | Helical compression spring |

We claim:

1. Process for the continuous production of absorbent bodies, especially tampons, preferably for feminine hygiene, comprising layering a continuous web of fibre material while moving said web in a direction of advance by folding said web about its longitudinal axis, said web is subsequently pressed radially by means of press rollers and thereafter is subdivided into length portions, wherein the web of fibre material is rolled down in steps in a plurality of successive press stages of rolling pressure at least to a final cross-section of the absorbent body and a fleece rod having an outer surface is formed thereby, before portions corresponding to the length of the absorbent body are subdivided.

2. Process according to claim 1 wherein the rolling pressure is exerted successively in steps in an inward pressing direction at each stage on diametrically opposed sides of the fleece rod, the pressing direction being mutually offset respectively at 90° about the fleece rod from stage to stage.

3. Process according to claim 1 wherein the fleece rod is rolled down to a cross-section which is smaller than the final cross-section of the absorbent body.

4. Process according to claim 2 wherein the fleece rod is provided with longitudinal grooves during the rolling.

5. Process according to claim 4 wherein the fleece rod is provided with two pairs of diametrically opposed longitudinal grooves.

6. Process according to claim 2 wherein the cross-section of the fleece rod is reduced first relatively sharply and then more slowly, before the outer surface of the fleece rod is smoothed and calibrated.

7. Process according to claim 1 characterized in that the fleece rod is heated during the press-rolling.

8. Process according to claim 1 wherein the fleece rod is guided positively between the successive press stages.

9. Process according to claim 1 wherein before the press-rolling, the web of fibre material is folded round onto itself several times from one longitudinal edge of the web in parallel with the longitudinal direction, before a second longitudinal edge of the web is laid round onto the multi-layered web of fibre material in an opposite direction.

10. Process according to claim 9 wherein the folded multi-layered web of fibre material has a rounded cross-section.

11. Process according to claim 10 wherein the web of fibre material has a width of 15-40 cm prior to the folding of the web.

12. Process according to claim 11 wherein before the press-rolling, the web of fibre material of round cross-section is surrounded by a liquid-permeable sheathing band with overlapping longitudinal edges.

13. Process according to claim 12 wherein the overlapping longitudinal edges of the sheathing band are connected to one another.

14. Process according to claim 13 wherein the longitudinal edges of the sheathing band are connected by the welding together of thermoplastic constituents of the sheathing band.

15. Process according to claim 13 wherein the sheathing band is a nonwoven web.

16. Process according to claim 15 wherein portions of the fleece rod which correspond to the length of an absorbent body are partially severed form one another by pinch-rolling the fleece rod diametrically and in a manner offset in steps at 90°, leaving a thin axial connecting web between the portions.

17. Process according to claim 16 wherein a front end of each length portion is formed into a dome-like shape during the pinching operation.

18. Process according to claim 16 wherein individual absorbent bodies are severed at the thin connecting web.

19. Process according to claim 16 wherein a hemispherical depression is formed in an end of the absorbent body as an insertion aid.

20. In an apparatus for making an absorbent body comprising means for supplying a continuous web of fibre material, a folding station with plates and rotatable discs for longitudinal folding of the web of fibre material, and a pair of press rollers followed by a cutting device, the improvement wherein the folding station is followed by a roller frame with a plurality of pairs of press rollers forming nips therebetween, the nips of the pairs of press rollers being reduced in steps and the press rollers rotating at a mean circumferential speed about axes of rotation.

21. Apparatus according to claim 20, characterized in that the pairs of press rollers are successively offset respectively at 90° relative to one another.

22. Apparatus according to claim 20 wherein the roller frame has three groups of a plurality of pairs of rollers, the nips of the first group of pairs of press rollers are successively reduced in steps greater than a reduction in the nips of the following second group of pairs of press rollers, and the third group of pairs of rollers have a constant nip size for smoothing.

23. Apparatus according to claim 20, wherein the circumference of each press roller is provided with at least one circumferential rib.

24. Apparatus according to claim 20 characterized in that guides fill interspaces between the successive pairs of rollers for the positive guidance of the fleece rod.

25. Apparatus according to claim 24 wherein the guides define a clear cross-sectional opening which is essentially elliptic, a major axis of the elliptic cross-section of each guide being arranged parallel to the axes of rotation of the respective preceding pair of rollers.

26. Apparatus according to claim 20 wherein the folding station is followed by an essentially conical guide tube for stabilizing a round cross-section of the multi-layered web of fibre material.

27. Apparatus according to claim 26 wherein the guide tube defines, on an underside, a longitudinal slot, in which a conveyor belt for the rounded web of fibre material is positioned.

28. Apparatus according to claim 27 including a continuous supply of liquid-permeable sheathing band and means for arranging the sheathing band between a top side of the conveyor belt and the rounded web of fibre material resting on it, so that the sheathing band is taken up in a conveying direction as a result of a frictional connection between the sheath and conveyor belt.

29. Apparatus according to claim 26 wherein a pair of drivable lead rollers are arranged on both sides of the guide tube for laying a U-shaped sheathing band onto an outer face of the guide tube in such a way that the sheathing band is conveyed slidably along on the outer face of the guide tube.

30. Apparatus according to claim 26 wherein the guide tube is positioned upstream from a first pair of rollers the guide tube having an introduction slot for each of two side tabs of a sheathing band, the introduction slots being offset axially in such a way that two side tabs of the sheathing band can be laid through the introduction slots onto the web of fibre material in the guide tube.

31. Apparatus according to claim 30 wherein the guide tube, in the region of the introduction slot, consists of individual distinct segments.

32. Apparatus according to claim 26 wherein there are means for supplying a sheathing band around the web and a closing device is arranged above a longitudinal slot in a top portion of the guide tube for closing and overlapping longitudinal edges of the sheathing band.

33. Apparatus according to claim 20 wherein after the roller frame there is positioned a severing station of at least two pairs of pinching rollers offset at 90° and having pinching projections for pinching off portions of the continuous web at intervals which correspond to a length of the absorbent body, so as to leave a thin axial connecting web between the portions of the continuous web.

34. Apparatus according to claim 33 wherein the pinching projections provide a front end of each of the absorbent bodies with in a dome-like shape.

35. Apparatus according to claim 34 wherein at least one pair of cutting rollers is provided at the end of the severing station for severing the thin axial connecting web between successive portions of the continuous web.

36. Apparatus according to claim 20 wherein the cutting device is followed by a dome-forming device for smoothing a preformed front end of the absorbent body.

37. Apparatus according to claim 36 wherein the dome-forming device includes an embossing device for forming a depression in a rear end of the absorbent body opposite said front end.

38. Apparatus according to claim 20 wherein a control device is provided for maintaining the same mean circumferential speed of all the pairs of press and smoothing rollers arranged in the roller frame.

* * * * *